United States Patent
Mayer et al.

(10) Patent No.: US 9,289,301 B2
(45) Date of Patent: Mar. 22, 2016

(54) METHOD FOR FASTENING AN IMPLANT TO BONE TISSUE AND CORRESPONDING IMPLANT SYSTEM

(71) Applicant: Woodwelding AG, Stansstad (CH)

(72) Inventors: Jorg Mayer, Niederlenz (CH); Andrea Mueller, Winterthur (CH)

(73) Assignee: WOODWELDING AG, Stansstad (CH)

( * ) Notice: Subject to any disclaimer, the term of this patent is extended or adjusted under 35 U.S.C. 154(b) by 197 days.

(21) Appl. No.: 13/724,251

(22) Filed: Dec. 21, 2012

(65) Prior Publication Data

US 2013/0123928 A1 May 16, 2013

Related U.S. Application Data

(62) Division of application No. 12/105,670, filed on Apr. 18, 2008, now Pat. No. 8,357,201.

(60) Provisional application No. 60/913,012, filed on Apr. 20, 2007.

(51) Int. Cl.
*A61F 2/30* (2006.01)
*A61B 17/68* (2006.01)
(Continued)

(52) U.S. Cl.
CPC ............... *A61F 2/30* (2013.01); *A61F 2/30721* (2013.01); *A61F 2/30749* (2013.01);
(Continued)

(58) Field of Classification Search
CPC ....... A61F 2/30; A61F 2/389; A61F 2/30749; A61F 2/30721; A61F 2/3804; A61F 2/42; A61F 2002/30332; A61F 2002/30457; A61F 2002/30616; A61F 2002/30777; A61F 2002/30845; A61F 2002/30892; A61F 2210/0071; A61F 2220/0058; A61F 2/30767; A61F 2/4081; A61F 2002/30065; A61F 2002/30382; A61F 2002/30604; A61F 2002/30772; A61F 2002/3082; A61F 2002/30878; A61F 2002/3412; A61F 2220/0033; A61B 17/68
See application file for complete search history.

(56) References Cited

U.S. PATENT DOCUMENTS 4,571,185 A 2/1986 Rota
4,761,871 A 8/1988 O'Connor et al.
(Continued)

FOREIGN PATENT DOCUMENTS

DE 20001940 5/2000
EP 0378928 7/1990
(Continued)

*Primary Examiner* — Gregory Anderson
*Assistant Examiner* — Son Dang
(74) *Attorney, Agent, or Firm* — Rankin, Hill & Clark LLP

(57) ABSTRACT

An implant designed e.g. as a replacement for an articulating surface of a human or animal joint is secured to the bone tissue with the aid of a plurality of fasteners (3). The implant (2) comprises a bone side to be brought into contact with the bone tissue, which bone side is equipped with a plurality of fastening structures restricted to this bone side. The fasteners (3) comprise a distal and a proximal side, wherein the distal side is equipped for being anchored in bone tissue and the proximal side is equipped for being connected with one of the fastening structures of the implant (2). The distal sides of the fasteners (3) are anchored in the bone tissue of the appropriately prepared bone and the implant (2) is then attached to the anchored fasteners (3) by connecting the fastening structures with the proximal sides of the fasteners (3), wherein the implant (2) is pressed against the proximal sides of the anchored fasteners (3). The connection between fastening structures and proximal sides of the fasteners is a positive fit connection, a material fit connection and/or a force fit connection.

29 Claims, 6 Drawing Sheets

(51) Int. Cl.
  *A61F 2/38* (2006.01)
  *A61F 2/40* (2006.01)
  *A61F 2/42* (2006.01)
  *A61F 2/34* (2006.01)

(52) U.S. Cl.
  CPC ........... *A61F 2/389* (2013.01); *A61B 17/68* (2013.01); *A61F 2/30767* (2013.01); *A61F 2/3804* (2013.01); *A61F 2/4081* (2013.01); *A61F 2/42* (2013.01); *A61F 2002/30065* (2013.01); *A61F 2002/3082* (2013.01); *A61F 2002/30332* (2013.01); *A61F 2002/30382* (2013.01); *A61F 2002/30457* (2013.01); *A61F 2002/30604* (2013.01); *A61F 2002/30616* (2013.01); *A61F 2002/30772* (2013.01); *A61F 2002/30777* (2013.01); *A61F 2002/30845* (2013.01); *A61F 2002/30878* (2013.01); *A61F 2002/30892* (2013.01); *A61F 2002/3412* (2013.01); *A61F 2210/0071* (2013.01); *A61F 2220/0033* (2013.01); *A61F 2220/0058* (2013.01)

(56) References Cited

U.S. PATENT DOCUMENTS

| | | |
|---|---|---|
| 4,769,040 A | 9/1988 | Wevers |
| 4,808,185 A | 2/1989 | Penenberg et al. |
| 4,936,847 A | 6/1990 | Manginelli |
| 4,964,865 A | 10/1990 | Burkhead et al. |
| 5,176,710 A | 1/1993 | Hahn et al. |
| 5,207,711 A | 5/1993 | Caspari et al. |
| 6,080,161 A * | 6/2000 | Eaves et al. .................. 606/76 |
| 6,087,903 A | 7/2000 | Kanno |
| 6,105,235 A | 8/2000 | Caldarise |
| 6,228,119 B1 | 5/2001 | Ondrla et al. |
| 6,527,809 B1 | 3/2003 | Doursounian et al. |
| 6,652,592 B1 | 11/2003 | Grooms et al. |
| 7,008,226 B2 | 3/2006 | Mayer et al. |
| 7,294,149 B2 | 11/2007 | Hozack et al. |
| 7,335,205 B2 | 2/2008 | Aeschlimann et al. |
| 7,625,408 B2 | 12/2009 | Gupta et al. |
| 7,628,819 B2 | 12/2009 | Gupta et al. |
| 8,690,951 B2 * | 4/2014 | Baum et al. ................ 623/19.11 |
| 2002/0049446 A1 | 4/2002 | Harkey, III et al. |
| 2004/0030341 A1 * | 2/2004 | Aeschlimann et al. ......... 606/72 |
| 2004/0260398 A1 | 12/2004 | Kelman |
| 2005/0125068 A1 | 6/2005 | Hozack et al. |
| 2006/0058883 A1 | 3/2006 | Aram et al. |
| 2006/0100714 A1 * | 5/2006 | Ensign ...................... 623/20.16 |
| 2007/0265704 A1 | 11/2007 | Mayer et al. |
| 2007/0270833 A1 | 11/2007 | Bonutti et al. |
| 2008/0021474 A1 | 1/2008 | Bonutti |
| 2008/0039845 A1 | 2/2008 | Bonutti et al. |
| 2008/0132947 A1 | 6/2008 | Mueller |
| 2009/0024161 A1 | 1/2009 | Bonutti et al. |
| 2010/0211120 A1 | 8/2010 | Bonutti et al. |
| 2013/0018478 A1 | 1/2013 | Hanssen et al. |

FOREIGN PATENT DOCUMENTS

| | | |
|---|---|---|
| FR | 2615726 | 12/1988 |
| JP | 2-232046 | 9/1990 |
| JP | 2005-511238 | 4/2005 |
| WO | 03/051211 | 6/2003 |
| WO | 2005079696 | 9/2005 |
| WO | 2008034277 | 3/2008 |
| WO | 2008116203 | 9/2008 |

* cited by examiner

METHOD FOR FASTENING AN IMPLANT TO BONE TISSUE AND CORRESPONDING IMPLANT SYSTEM

BACKGROUND OF THE INVENTION

The invention lies in the field of medical engineering and concerns a method for fastening an implant to human or animal bone tissue as well as a corresponding implant system, wherein the implant may be designed e.g. as a replacement for the articulating surface of a joint, as a replacement for a larger bone section or another tissue or as an element for stabilizing a bone e.g. damaged by fracture. The invention further concerns a kit for carrying out the method.

Replacements of articulating surfaces of human joints are known, in particular, in connection with the tibia plateau in the knee joint (articulating surface with concave and convex portions), the glenoid cavity on the shoulder-blade and the acetabulum on the pelvis (concave articulating surfaces), but are also used for articulating surfaces of other joints (elbows, wrists, ankles or digital joints), in particular also convex articulating surfaces such as e.g. the articulating surface of the femoral head.

Known implants replacing articulating surfaces of joints (resurfacing implants) are flattish elements having a thickness which is smaller than their dimensions parallel to the bone surface and a concave and/or convex form and they usually comprise an essentially centered shaft or comb facing the bone tissue. These implants consist e.g. of a metal (e.g. titanium, titanium alloys or CoCr cast alloys) and carry on their side, facing the joint a bearing element, constituting the actual articulating surface and usually consisting of a synthetic material (e.g. polyethylene, in particular UHMWPE or ultra high molecular weight polyethylene). According to the state of the art, the implant is secured in the cancellous bone tissue of the appropriately prepared bone by means of a bone cement, by means of inserting screws into the bone through corresponding bores in the implant and/or by means of the shaft or comb being malleted into a corresponding opening in the bone tissue to achieve a press fit. It is further suggested to secure resurfacing implants not in the bone tissue beneath the implant, but in the cortical bone next to the implant, e.g. by clamping or screwing.

All named methods for securing resurfacing implants suffer specific disadvantages. The use of bone cement does not allow significant osseointegration, which would be advantageous for a durable connection. Screws extending through the implant require through bores and these bores and, subsequently, the heads of the screws inserted therein constitute friction points on the joint side of the implant, which is particularly detrimental if the implant constitutes the articulating surface (without bearing element) and the bores therefore are part of the articulating surface. Such friction points may also reduce the lifespan of a bearing element if it is movable on the joint side of the implant, as is usually the case for tibia plateau implants. Although securement by press fit permits osseointegration, it gives only a limited primary stability and, thus, necessitates a prolonged period of rest for the repaired joint. The above mentioned lateral securing requires additional space and therefore cannot be applied universally.

The implants for the replacement of larger bone parts or other tissues mentioned above in addition to the resurfacing implants may e.g. replace a complete joint ball including the neck. Such implants usually comprise a lengthy shaft to be secured in the marrow space of a tubular bone, again with the aid of a cement or with the aid of a press fit. According to the state of the art, implants for supporting or stabilizing bones e.g. damaged by fracture are often plates or rods with through bores to be attached to the bone e.g. by means of screws. In many of these cases the same aforementioned disadvantages of the named fastening methods apply.

BRIEF SUMMARY OF THE INVENTION

For the reasons mentioned above an alternative way for fastening implants on human or animal bone tissue is desirable, wherein this fastening does not, or does at least to a greatly reduced extent only, have the above mentioned disadvantages. Thus the object of the invention is to create such an alternative fastening of implants on bone tissue, in other words, to create appropriately equipped implant systems and a method for fastening these on appropriately prepared bone tissue. Therein the implant system according to the invention is to enable osseointegration, the implant side facing away from the bone tissue is to comprise as few structures serving the fastening function as possible, and the fastening method is not to be more elaborate than known methods serving the same purpose.

In the following, the expression bone tissue does not only relate to purely native bone tissue but also to bone tissue reinforced by injection of a cement based on calcium phosphate (osteoplasty, in particular vertebroplasty), and to bone tissue augmented with the aid of a bone replacement material.

The implant of the implant system according to the invention comprises fastening structures (e.g. recesses and/or protrusions) on its one surface which is to come into contact with the bone tissue. The implant system further comprises a plurality of fasteners, which, on a distal side, are equipped for being anchored in the bone tissue and, on a proximal side, for being connected with the fastening structures of the implant. Each fastener is essentially assigned to one of the fastening structures and the fasteners are e.g. pin-shaped.

The implant according to the invention is fastened to the appropriately prepared bone tissue in two steps. In an anchoring step, the fasteners are anchored in the prepared bone. In a fastening step, the implant is attached to the proximal sides of the fasteners anchored in the bone, by means of the fastening structures, wherein the implant is pressed against the proximal sides of the fasteners. Therein the fastening step is performed preferably after the anchoring step. For anchoring the fasteners, use of a corresponding template ensures that the positions of the anchored fasteners correspond with the positions of the fastening structures on the bone side of the implant. Advantageously, the anchoring of the fasteners is performed in sequence but the attachment of the implant to all fasteners essentially simultaneously. In specific applications of the method according to the invention it is also possible to execute only a part of the anchoring step (e.g. positioning of the fasteners in corresponding openings) prior to the fastening step and subsequently effect the proper anchoring simultaneously with the fastening step.

In the method according to the invention, the connection to be established between the proximal sides of the fasteners and recesses or protrusions of the implant serving as fastening structures may be a positive fit connection, a force fit connection and/or a material connection. The connection must be of such a design that it can be achieved from a side of the implant other than the implant side which is to be brought into contact with the bone tissue (in the case of flattish and accordingly accessible implants advantageously from the opposite implant side) and, if at all possible, simultaneously for all fasteners. Such a connection is produced e.g. by a snap action between two parts correspondingly adapted to each other (positive fit connection) as known from fastening dentures on tooth stumps or dental implants. A positive fit connection can also be produced by melting or at least softening a thermoplastic material on one side and embedding this material in undercut recesses on the opposite side, wherein the energy required for liquefaction is supplied to the thermoplastic material through the implant by heating suitable areas of the implant or by transmitting mechanical vibration to the implant. A material connection is achieved e.g. by fusing thermoplastic material provided on both sides, wherein the required energy is supplied to the thermoplastic material in the same manner. For a force fit connection the fasteners comprise e.g. conic openings and the fastening structures of the implant consist of tapered protrusions adjusted to the conic openings in such a manner that they can be pressed into the openings and are, thus, held by a self-locking press fit. In all cases, the implant is advantageously pressed against the proximal sides of the anchored fasteners with the aid of a correspondingly adapted pressing tool, which may be further equipped for transferring energy (e.g. heat or mechanical vibration) to the implant.

For being anchored in the bone tissue, the fasteners preferably comprise a thermoplastic material on their distal side so that they can be anchored in the bone tissue by means of mechanical oscillation (advantageously ultrasonic vibration), as is known e.g. from the publications U.S. Pat. No. 7,335,205, U.S. Pat. No. 7,008,226, WO-2005/079696, or WO-2008/034277. For such an anchoring it is advantageous, but not necessary, to create, in the bone, openings which are adapted to the fasteners. Alternatively, the distal sides of the fasteners may be screw-like, comprising e.g. self-tapping threads to be screwed into the bone tissue, wherein openings for accommodating the screws may or may not be drilled into the bone beforehand. Fasteners with pointed distal sides and barbs are also conceivable, such fasteners being anchored simply by being malleted into the bone tissue. In principle, any known anchoring methods or combinations thereof are suitable for anchoring the fasteners in the bone, in particular anchoring methods which are suitable for anchorage in cancellous or even osteoporotic bone tissue, as is in particular the case for the first named anchoring method. Therein it is also possible to anchor the fasteners in corresponding openings in the bone tissue with the aid of bone cement.

In most embodiments of the method according to the invention, the step of anchoring the fasteners and the step of connecting the implant with the anchored fasteners are essentially independent of each other and are executed after each other. Therefore, different embodiments of these two steps as well as different embodiments of proximal and distal sides of the fasteners can be combined in an essentially freely selectable manner. Particularly advantageous embodiments result from combinations of two steps which can be carried out with simple fasteners and/or with fasteners whose height relative to the prepared bone surface after anchoring can be adjusted by simple means so that only a limited accuracy is required for the anchoring step.

A kit for the execution of the method according to the invention comprises the implant system (implant and a plurality of appropriate fasteners) as well as at least one tool adapted to the implant and/or to the fasteners. The tool is in particular a template enabling anchoring of the fasteners at the positions of the bone tissue corresponding with the positions of the fastening structures on the implant and/or a tool for pressing the implant against the proximal fastener sides.

If the implant, according to the invention, is a resurfacing implant it has a flattish shape with a bone side to be brought into contact with the bone tissue and a joint side opposite the bone side, i.e. facing the joint. The joint side is equipped for mounting a bearing element thereon in a per se known manner e.g. by snapping the bearing element in beneath an appropriate implant rim or, in the case of a tibia plateau, on to a post which is movable to a limited degree in relation to the flat implant part. On the other hand, the joint side of the resurfacing implant may have a surface which is suitable as an articulating surface. Advantageously, the joint side of the implant does not comprise any structures serving the securement of the implant to the bone. These fastening structures are present on the bone side of the implant, e.g. in the shape of a number of recesses and/or protrusions. Portions of the implant bone side between fastening structures which after implantation remain in close contact with the bone tissue are preferably equipped in a per se known manner for enhancing osseointegration. Resurfacing implants according to the invention can essentially be used for resurfacing all articulating surfaces of human and animal joints, in particular for the applications mentioned above in connection with the state of the art.

BRIEF DESCRIPTION OF THE DRAWINGS

Exemplary embodiments and applications of method and implant system according to the invention are described in more detail in connection with the following Figs., wherein.

DETAILED DESCRIPTION OF THE INVENTION

Figure 1A:
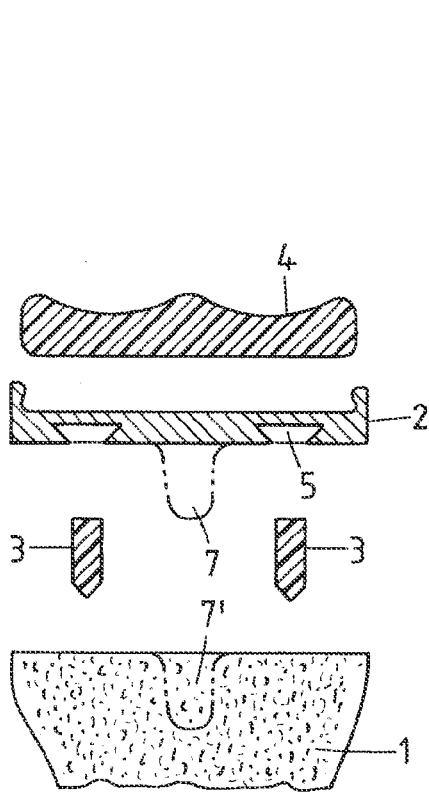
FIG. 1A-1C illustrate a first exemplary embodiment of the method according to the invention using the example of resurfacing a tibia plateau, wherein the fasteners are anchored in openings provided in the bone tissue by means of a thermoplastic material and mechanical oscillation and wherein the implant is connected in situ with the fasteners by a positive fit connection achieved by melting or softening a thermoplastic material.
Figure 1C:
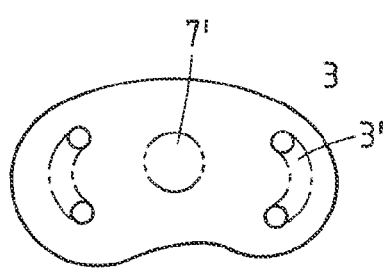
Figure 1B:
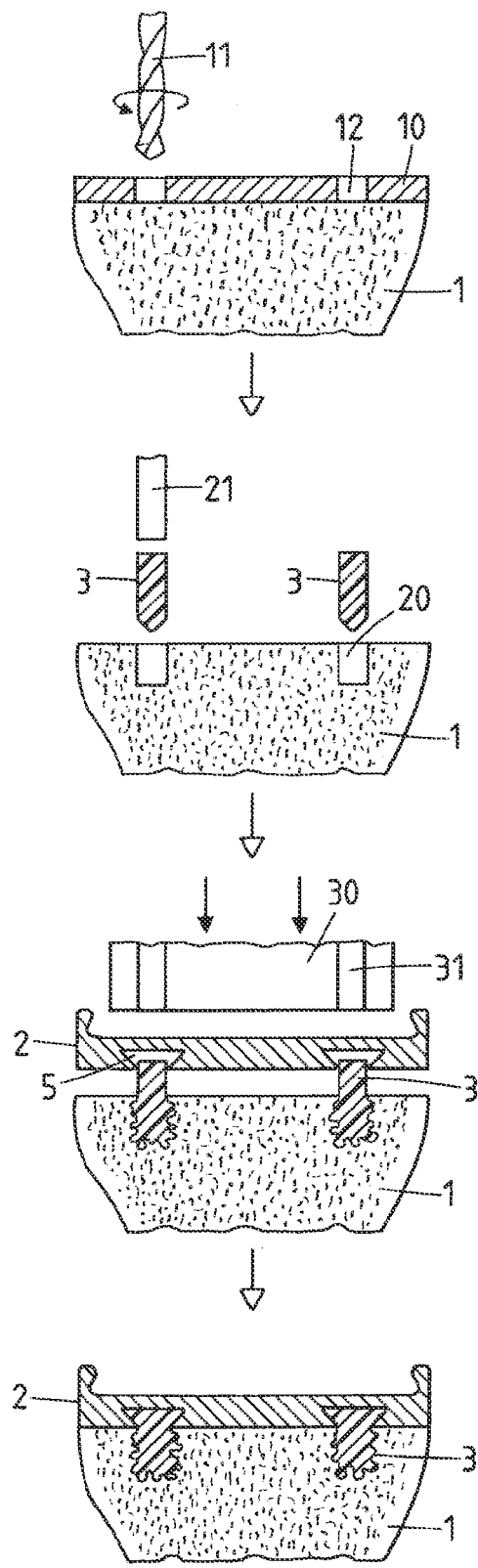

FIGS. 1A, 1B and 1C illustrate a first exemplary embodiment of the implant system and of the method for fastening the implant according to the invention. These Figs. illustrate the resurfacing of a tibia plateau (articulating surface) as an exemplary application. As already mentioned above, implant and method according to the invention are not only suitable for the resurfacing of a tibia plateau but essentially for any replacement of an articulating surface of a human or animal joint, wherein each specific application requires a corresponding adaptation of the implant regarding, in particular, shape and design of the joint side and a corresponding adaptation of the fasteners regarding number, dimensions and positions in relation to the bone and the implant. The named adaptations can be carried out by one skilled in the art without any problem. Implant and method as illustrated in FIGS. 1A to 1C are also suitable for supporting or stabilizing bones (e.g. after a fracture), wherein in such a case the implant is fashioned as plate or rod and is usually secured in cortical bone tissue with the aid of the fasteners.

FIG. 1A shows in section the tibia bone 1 prepared for resurfacing in a generally known manner, the implant 2 having a generally flat form, and a plurality of fasteners 3, of which e.g. four are required for securing the tibia plateau implant (FIG. 1C shows exemplary positions of the fasteners on the tibia plateau which is viewed from the top). A bearing element 4 to be locked into the implant on the joint side thereof is also shown.

The implant 2 consists in a generally known fashion e.g. of a metal (e.g. titanium, titanium alloy, CoCr cast alloy), of a ceramic material (e.g. aluminum oxide or zirconium oxide), of a composite material (e.g. filled PEEK) or of a high strength plastic material without filler (preferably cristalline polymer having a glass transition temperature above 100° C. or thermosetting plastic). The fastening structures provided on the bone side of the implant 2 are in the present case undercut recesses 5, their positions determining the anchoring positions of the fasteners 3.

In the embodiment according to FIG. 1A, the fasteners 3 are simple pins of a medically acceptable material with thermoplastic properties. Their proximal ends are adapted to the entrance of the recesses 5 and their distal ends are e.g. pointed or tapering.

FIG. 1B illustrates four consecutive phases of the method according to the invention, wherein the implant system according to FIG. 1A is attached to the end of the tibia bone 1 facing the knee-joint.

First, openings 20 for anchoring the fasteners 3 in the bone tissue 1 are produced, advantageously using a template 10 and a drilling tool 11. The shape of the template 10 corresponds (in particular on the bone side) with the implant 2 and comprises bores 12 in positions (FIG. 1C) corresponding with the positions of the recesses 5 in the implant, the diameter of which bores is adapted to the diameter of the drilling tool 11. The template 10 is secured on the prepared bone surface with suitable means and the openings 20 are made by moving the drilling tool 11 through the bores 12. Advantageously, the drilling tool 11 comprises generally known means for setting a required depth for the openings 20.

When the openings 20 are made, the template 10 is removed and one after the other of the fasteners 3 is anchored in the openings, wherein each one the fasteners are positioned in one of the openings and is then pressed into the opening 20 while simultaneously being vibrated with the aid of an oscillating tool 21 (e.g. sonotrode of an ultra-sonic device with a distal coupling surface adapted to the proximal face of the fastener 3). The friction between the surface of the fastener 3 and the bone tissue at the bottom and/or wall of the opening 20 caused by the oscillation leads to the thermoplastic material of the fastener 3 being liquefied and being pressed into the bone tissue in liquid form, while the fastener 3 is simultaneously advanced in the opening 20. When the fastener 3 is sufficiently advanced in the opening 20, i.e. when a sufficient amount of thermoplastic material has been pressed into the bone tissue, the oscillation is stopped so that the liquefied material penetrating the bone tissue re-solidifies and the fastener 3 is, thus, anchored in the bone tissue essentially by a positive fit connection. FIG. 1C shows four fasteners 3 anchored in the bone tissue.

Once all the fasteners 3 are anchored, the implant 2 is positioned on the fasteners 3 in such a way that the proximal sides of the fasteners 3 which protrude from the bone tissue, are positioned in the recesses 3. The implant 2 is then pressed towards the bone surface with the aid of a pressing tool 30 the face of which is adapted to the joint side of the implant 2, while heat is supplied in a suitable manner (e.g. via heat conductor or heating elements 31) to the implant areas corresponding with the fastener positions. The proximal ends of the fasteners 3 are pressed into the recesses 5 by the pressure from the pressing tool 30 being pressed against the implant 2, or against the fasteners 3 respectively. The thermoplastic material of the fasteners yields through the contact with the locally heated implant and adapts in form to the undercut shape of the recesses 5, thus creating the desired positive fit connection between implant 2 and fastener 3.

The completed securement of the implant 2 in the bone 1 is shown at the bottom of FIG. 1B. Preferably, in particular for a resurfacing implant, the length of the fasteners 3 is such that the bone side of the implant 2, as illustrated at the bottom in FIG. 1B, touches the bone tissue between the fasteners 3. This enables osseointegration of the implant whose surface facing the bone is pre-treated accordingly (e.g. roughened surface of titanium or titanium alloy or a surface carrying a coating based on calcium phosphate).

Suitable materials with thermoplastic properties for the fasteners 3 according to FIGS. 1A and 1B are e.g.: resorbable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable polymers such as polyolefines (e.g. polyethylene), polyacrylates, polymethacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene. An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec)

The thermoplastic materials may contain foreign phases or compounds serving further functions. In particular, the thermoplastic material may be strengthened by admixed fibers or whiskers (e.g. of calcium phosphate ceramics or glasses) and such represent a composite material. The thermoplastic material may further contain components which expand or dissolve (create pores) in situ (e.g. polyesters, polysaccharides, hydrogels, sodium phosphates) or compounds to be released in situ and having a therapeutic effect, e.g. promotion of healing and regeneration, e.g. growth factors, antibiotics, or inflammation inhibitors. Furthermore, buffers such as sodium or calcium phosphate or calcium carbonate may be contained in resorbable thermoplastic materials against adverse effects of acidic decomposition as described e.g. in Heidemann et. al. "pH-stabilization of predegraded PDLLA by an admixture of water-soluble sodiumhydrogenphosphate", Biomaterials 2002, September; 23(17):3567-74. If the thermoplastic material is resorbable, release of such compounds is delayed.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel).

Osseointegration stimulating fillers that are only partially or hardly degradable, for non degradable polymers include: Bioglasses, Hydroxyapatite (>90% cristyllinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20.

Embodiments of bioactive fillers and their discussion can for example be found in X. Huang and X. Miao, J Biomater App. 2007 April; 21(4):351-74), J A Juhasz et al. Biomaterials, 2004 March; 25(6):949-55.

Particulate filler types include: coarse type: 5-20 μm (contents, preferentially 10-25% by volume), sub-micron (nano-fillers as from precipitation, preferentially plate like aspect ratio>10, 10-50 nm, contents 0.5 to 5% by volume).

For the fasteners being anchored as discussed above, it is advantageous for the thermoplastic material to have a modulus of elasticity of more than 0.5 GPa, i.e. to be able to transmit the mechanical vibration which usually has a frequency in the range of 2 to 200 kHz with little damping from the proximal face to the surfaces which are in contact with the bone tissue. For keeping the thermal load within an acceptable range, the material liquefies at a temperature of less than about 350° C. For initiating and/or facilitating liquefaction in the named contact areas it may be advantageous to provide in these contact areas a preferably thin contact layer of a "softer" material which dampens the mechanical vibration more and therefore is more easily heated and therewith liquefied. Suitable measures and materials for providing such contact layers are described in the co-pending U.S. application No. 60/888,798, which is incorporated herein by reference. For thermoplastic material of a high cristallinity such as e.g. polyether aryleketones (PEEK or PEAK) or PLLA anchorage in the above described manner is hardly possible without the named contact layer.

The embodiment of the invention as shown in FIGS. 1A and 1B comprises the following advantages:

The anchoring by means of thermoplastic material and mechanical oscillation is suitable in particular for anchorage in bone tissue with little stability (cancellous or osteoporotic bone tissue).

The form requirements for the proximal side of the fasteners 3 are minimal (they must be capable of being inserted into the recesses 5), so that these sides can be trimmed subsequent to anchoring in order to compensate for differing anchoring depths of individual fasteners 3 due to differing bone qualities. Such trimming is very simple as a superfluous length of a fastener can e.g. simply be cut off.

The recesses 5 being designed to be at least slightly larger than the proximal ends of the fasteners allow at least to a modest degree for an adjustment of the implant's lateral position subsequent to the anchoring of the fasteners.

The fasteners 3 may comprise any chosen, in particular non-circular cross-section that can be adapted to the osseous conditions and/or to the load distribution over the articulating surface to be resurfaced.

The fasteners 3 may fulfill further functions in addition to the implant securement, in particular reinforcement of bone tissue with little stability, repair of lacerations in the bone tissue, or fastening of bone fragments or augmentation materials.

The implant system as well as the method according to FIGS. 1A to 1C can be modified in widely differing ways. Some examples follow:

The recesses 5 are situated in protrusions of the bone side of the implant and the entrances of the openings 20 comprise a corresponding width (similar to the embodiment according to FIG. 2) such that the protrusions can be positioned therein.

Figures 6, 7:
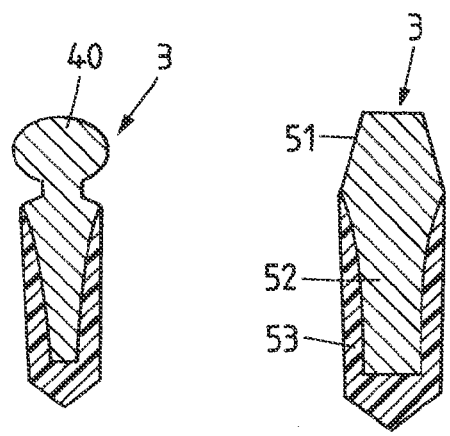
FIGS. 6 and 7 show further embodiments of fasteners suitable for the fastening according to FIG. 2 or FIG. 3 respectively.

The fasteners 3 do not consist entirely of the thermoplastic material but comprise a core of metal, of ceramic, of a thermoplastic material which does not liquefy under the implantation conditions, or of a thermosetting plastic material, wherein the surface of this core is completely or just partly covered with the liquefiable thermoplastic material (for an example see FIGS. 6 and 7). The fasteners may also comprise a non-liquefiable sheath in which the liquefiable material is placed, and from which it is squeezed out through appropriate openings in the sheath and into the bone tissue when the vibration is applied and the material is therewith liquefied. As a liquefiable material, a thermoplastic polymer or a polymer, ceramic or hydraulic cement with thixotropic properties (e.g. Norian® of Synthes or Sulfix® of Centerpulse) may be provided in the sheath (for an example see FIGS. 11 and 13).

The core or sheath mentioned above may comprise surface areas remaining free of the liquefiable material and being equipped for enhancing osseointegration and/or comprising self-cutting edges as disclosed in the publications U.S. Pat. No. 7,008,226 and WO-2005/079696 which are enclosed herein by reference.

The core or sheath of the fastener comprises the undercut cavity and the implant part comprises protrusions of the thermoplastic material serving as fastening structures.

The thermoplastic materials of distal and proximal sides of the fasteners 3 are different.

The fasteners 3 are pins with a cross-section other than round, so that a means other than the above described drilling tool 11 is to be provided for producing the openings 20.

The fasteners 3 are not pin-shaped but have the shape of tongues or blades extending e.g. parallel to the rim of the implant 2 as illustrated in FIG. 1C in dash-dot lines and denominated with 3'.

Fasteners 3 of different shapes and/or dimensions are provided for positions of different load levels upon the articulating surface.

The fasteners 3 are not anchored in the openings 20 by means of mechanical oscillation but with the aid of a curable bone cement.

The fasteners 3 are slim and pointed and they are anchored in the bone tissue with the aid of mechanical oscillation and pressure without providing openings 20 (or providing only partial openings, e.g. only through a cortical bone layer).

The implant may also comprise, in a per se known fashion, a shaft 7 (indicated by a dash-dot-line in FIG. 1A) or comb on its bone side to be positioned in a corresponding shaft opening 7' situated in the bone tissue. Such a shaft or comb, provided according to state-of-the-art technology for the absorption of shearing stress is however not necessary according to the invention as such shearing stress is easily absorbed by the fasteners 3.

Figure 5:
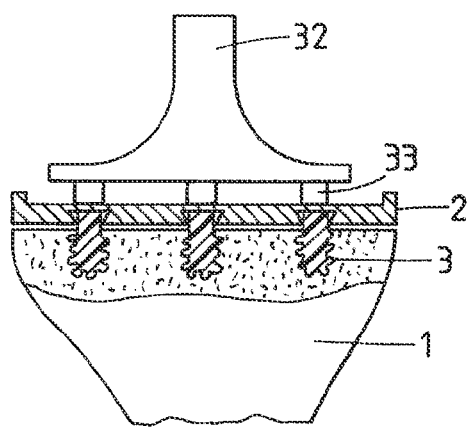
FIG. 5 shows a further embodiment of the method and a tool for fastening the implant to the fasteners, where implant and fasteners are the same as illustrated in FIG. 1A.

Instead of the heat supply, mechanical oscillation may be coupled into the implant for heating the proximal ends of the implant's joint side. To this end e.g. an oscillating tool 32 is used as shown in FIG. 5. This tool is e.g. part of an ultrasonic device and comprises a distal end with oscillating extensions 33, the positions of which are adapted to the positions of the fasteners.

Figure 12:
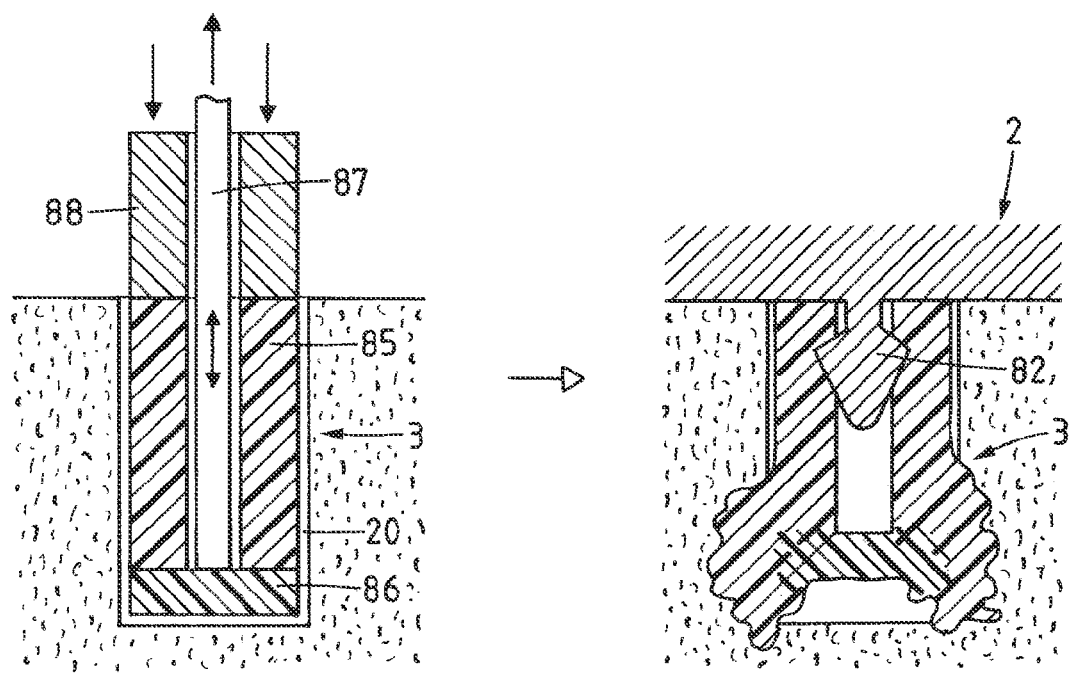

The fasteners 3 are anchored in openings with the aid of a thermoplastic material and mechanical oscillation, wherein the proximal side of the fastener is kept at a predetermined position relative to the bone surface. An example of such a anchoring procedure is illustrated in FIG. 12. Further embodiments are described in the co-pending U.S. application No. 60/983,791, which is enclosed herein by reference.

Figure 13:
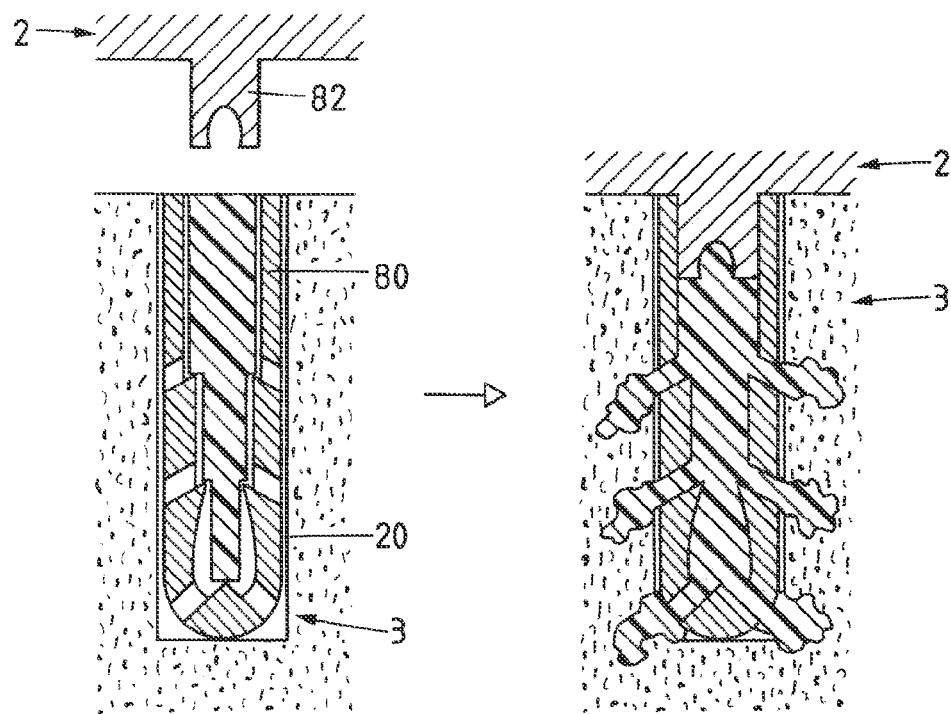

The fasteners are only positioned in the openings 20 prior to the fastening step, wherein anchoring of the fasteners and fastening of the implant to the proximal fastener sides is achieved simultaneously by coupling mechanical vibration into the implant (see FIG. 13).

Figure 2:
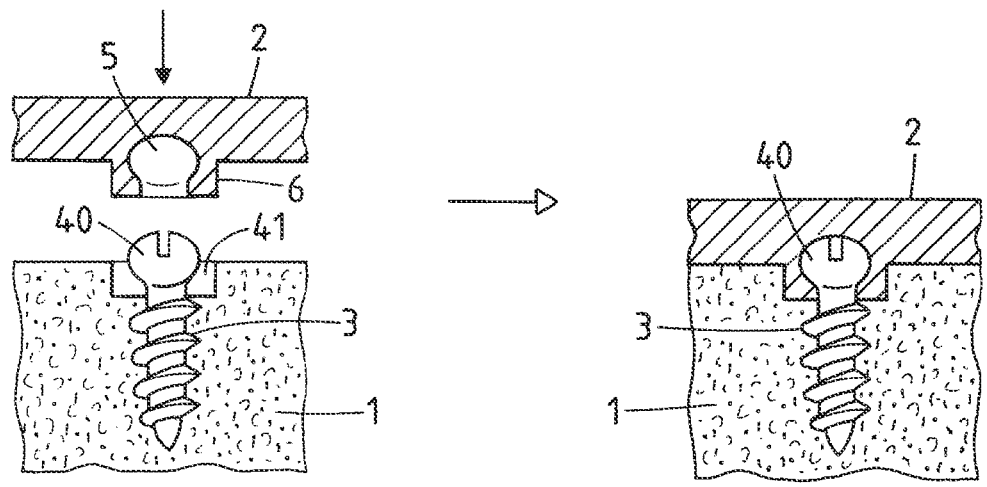
FIG. 2 shows a further exemplary embodiment of fastening structure and fastener, wherein a snap connection is provided between the two and wherein the fastener is anchored in the bone tissue by means of a screw thread.

FIG. 2 shows a further exemplary embodiment of a connection between an implant 2 and a fastener 3 suitable for the implant system according to the invention and of a suitable anchoring of the fastener 3 in the bone tissue 1, wherein just a section of the implant 2 and a single fastener 3 are shown in an axial section and wherein the implant is fashioned once more as a flattish or flat implant e.g. a resurfacing implant. The left-hand side of FIG. 2 illustrates the fastener 3 already anchored and the implant 2 prior to being attached to the fastener. The right-hand side illustrates the implant after the fastening step.

Again, the implant 2 comprises, as fastening structures, undercut recesses 5 which are situated e.g. in protrusions 6. The fastener 3 comprises a screw-shaped distal side and a proximal head 40 equipped for being coupled to a screw driving tool (e.g. comprising an outer or inner hexagon or a slot) and being adapted to the recess 5. Protrusion 6 and/or head 40 are sufficiently elastic to allow for the head 40 to snap into the recess 5. In order to establish contact for osseointegration between the surface of the bone side of the implant 2 and the bone surface, the opening to be provided in the bone tissue 1 for receiving the fastener 3 comprises an entrance 41 which is adapted to the protrusion 6. From this entrance 41, a bore may be provided for the screw or the screw may be screwed into the bone tissue 1 without prior drilling.

Instead of the protrusion 6 with recess 5, a head constituting the fastening structure may be provided on the implant, whilst the fastener is equipped with an undercut recess adapted to this head. Instead of the distal side of the fastener being designed as a screw, it may also, at least in part, comprise a surface of a material with thermoplastic properties suitable for anchorage with the aid of ultrasonic vibration. An example of such a fastener is illustrated in FIG. 6.

Figure 3:
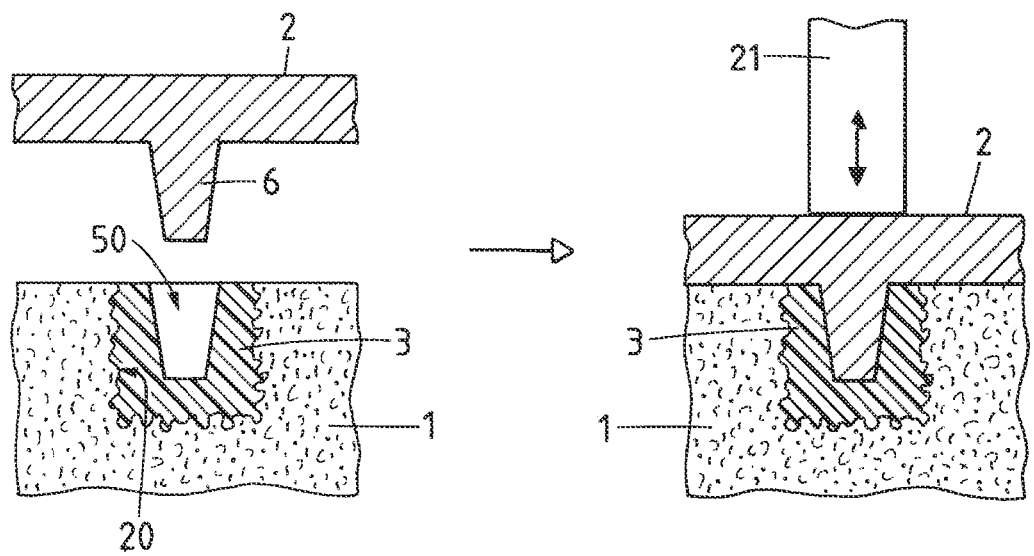
FIG. 3 shows a further exemplary embodiment of fastening structure and fastener, wherein a force fit connection is provided between the two and wherein the fastener is anchored in the bone tissue by means of a cement or by means of a thermoplastic material and mechanical oscillation.

Similar to FIG. 2, FIG. 3 shows a further connection between implant 2 and fastener 3 suitable for the implant system according to the invention and a suitable anchoring of the fastener 3 in the bone tissue 1. The implant is again of a flattish shape and therefore is e.g. suitable for resurfacing the articulating surface of a joint.

Again, the fastener 3 consists e.g. at least in part of a thermoplastic material liquefiable by mechanical oscillation and is anchored in a corresponding opening 20 in the bone tissue 1 by means of mechanical oscillation, as described for the embodiment according to FIGS. 1A to 1C. The fastener comprises a conical opening 50 adapted to a corresponding and equally conical protrusion 6 on the bone side of the implant 2, so that the protrusion 6 can be pressed into the opening 50 to be retained therein by a force fit connection (press fit). Such pressing-in can indeed be all that is required for the securing step. If applicable, the connection between the walls of the opening 50 and the protrusion 6 may be reinforced by ultrasonic welding. In such a case the conic protrusion 6 or at least the surface thereof must also consist of a thermoplastic material, which is capable of being fused to the thermoplastic material of the fastener 3. Such welding can be achieved by applying an oscillation tool 21 on the joint side of the implant 2 opposite the protrusion 6, as indicated on the right-hand side of FIG. 3. It is also possible to coat just one side (cone 6 or conical 50 opening) with a thermoplastic material and equip the opposite side with surface structures to be penetrated by the thermoplastic material when it is liquefied by oscillation, which results in a positive fit connection.

A similar connection between implant 2 and fastener 3 as illustrated in FIG. 3 is achieved if the conical opening is situated on the implant and the cone on the fastener 3. Such a fastener 3 is illustrated in FIG. 7. The cone 51 and a core 52 extending to the distal side of the fastener 3 consist e.g. of a metal and the core 52 is at least partly surrounded by the thermoplastic material 53.

Figure 4:
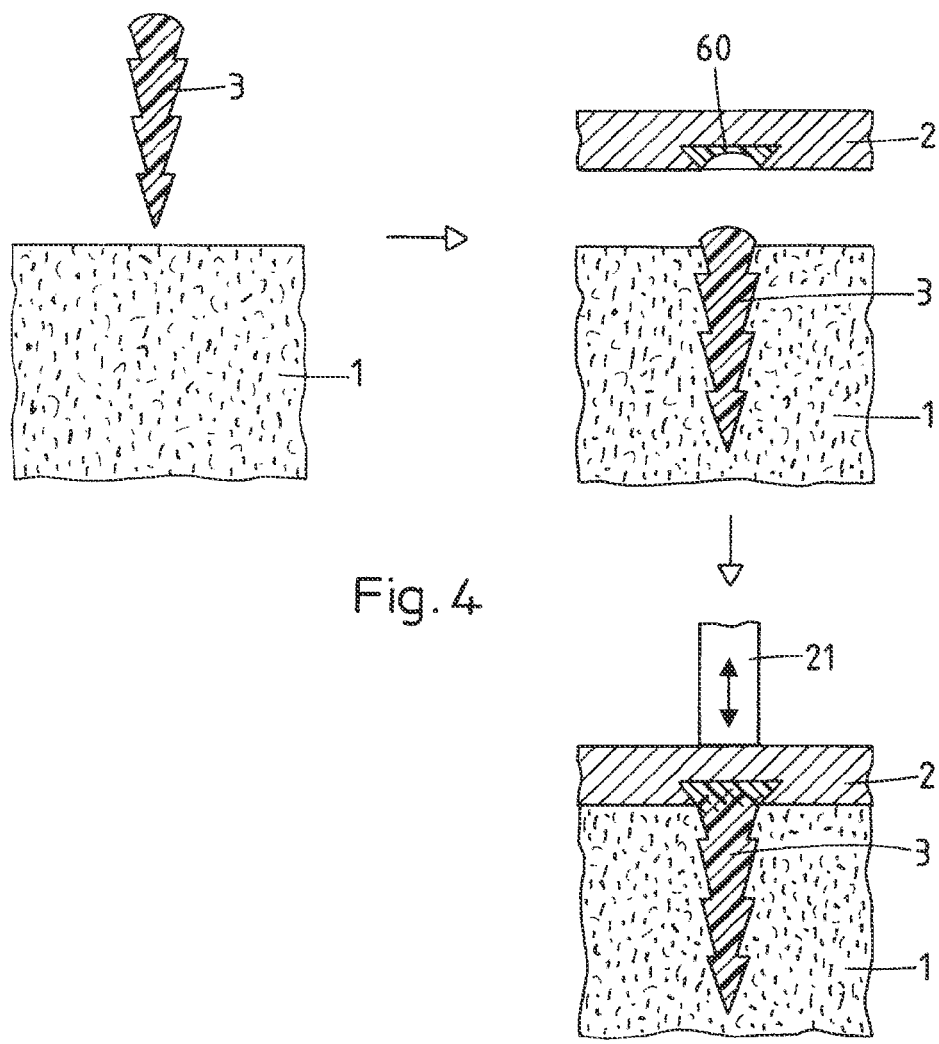
FIG. 4 shows a further exemplary embodiment of fastening structure and fastener, wherein a weld (material connection) is provided between the two and wherein the fastener is anchored in the bone tissue by being malleted into the bone tissue.

FIG. 4 shows a further connection between implant 2 and fastener 3 which is suitable for the method according to the invention and the anchoring of the fastener 3 in the bone tissue 1, again assuming a flattish implant e.g. a resurfacing implant.

The fastener 3 comprises at least on its proximal side a material with thermoplastic properties and is shaped like an anchor equipped with a sharp point and cutting edges, and possibly with structures acting as barbs. The fastener 3 is anchored by being malleted into the bone tissue 1. As fastening structures on its bone side, the implant 2 comprises locations 60 consisting of a material which is capable of being fused with the thermoplastic material of the fastener 3. Advantageously, the proximal side of the fastener 3 and the locations 60 are designed for self-centering so that they mesh at least slightly (e.g. slightly concave and convex respectively, as illustrated). For connecting the implant 2 with the fastener 3, an oscillating tool 21 (e.g. sonotrode of an ultrasonic device) is applied to the joint side of the implant 2, wherein the positions of the locations 60 are advantageously marked accordingly.

Figure 14A:
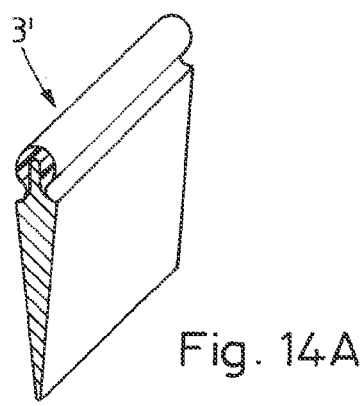
FIGS. 14A to 14C show further exemplary fasteners and fastener assemblies suitable for the implant system according to the invention.

The fastener 3 according to FIG. 4 may be pin-shaped, but may, in particular, also be shaped as a blade (see FIG. 14A).

Figure 8:
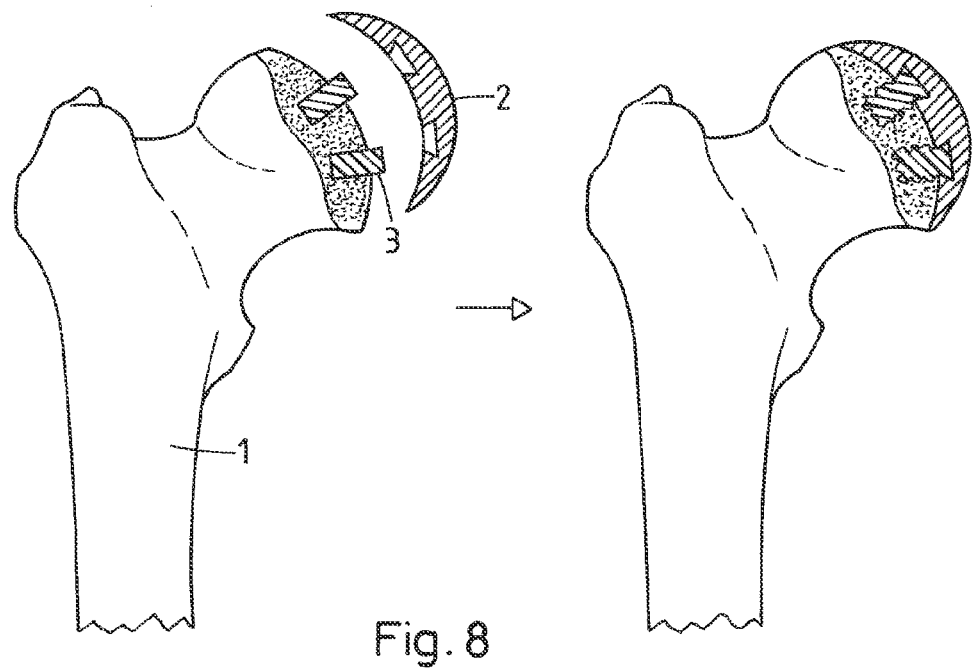
FIGS. 8 to 10 show further embodiments of method and implant system according to the invention.

FIG. 8 illustrates, highly schematically, a further exemplary embodiment of the implant system according to the invention. It serves for resurfacing a femoral head (convex articulating surface). All embodiments of the invention illustrated in the previous FIGS. 1 to 7 can also be applied to this case. Similarly, implants having the shape of plates or rods can be secured to a bone, the plates or rods having supporting and stabilizing functions e.g. in the case of bone fractures. In contrast to the resurfacing implants which are attached to mainly cancellous bone tissue, the named plates and rods are usually fixed to cortical bone tissue and usually no osseointegration is desired on the bone side of the implant.

The implants hitherto described are of a flattish shape and the implant side facing the bone tissue is essentially accessible for the application of tools. However, the method according to the invention is also applicable when this is not the case. Examples of such applications are intervertebral disc implants to be introduced between two vertebrae and to be secured to at least one of them or implant shafts to be secured in a tubular bone such as e.g. the shaft of a hip joint prosthesis. The same may apply for a joint resurfacing implant, in particular for a tibia plateau implant, if the implant is introduced into the knee joint without making the tibia end fully accessible.

Figure 9:
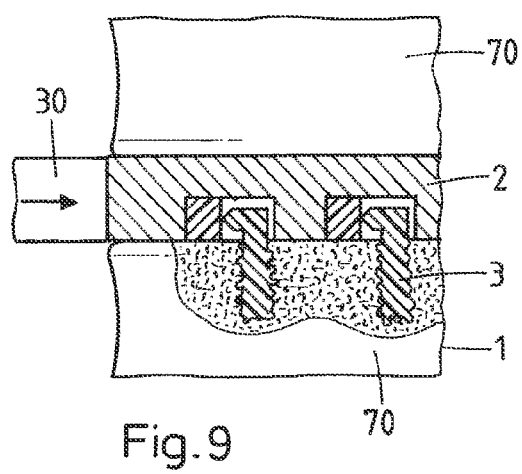
Figure 10:
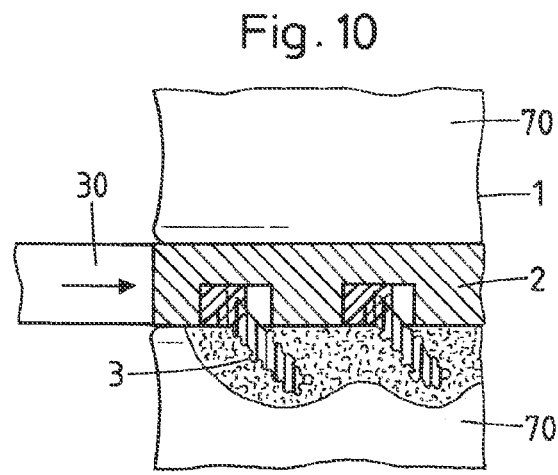

FIGS. 9 and 10 illustrate two embodiments of the implant system according to the invention which are suitable for the above named applications, in particular if access to the implantation site is limited, such that the implant needs to be moved into its implanted position in a direction which is not perpendicular but substantially parallel to the bone surface to which the implant is to be fastened and such that access to the side opposite the bone side of the implant is limited or not possible. The procedure of anchoring the fasteners 3 and the means and ways for establishing the connection between the fasteners and the fastening structures of the implant are substantially the same as described above and therefore need not be described in detail again.

FIG. 9 illustrates a vertebral disc implant 2. The fasteners 3 are anchored in the upper (and/or lower) side of a vertebral body 70. For positioning and securing the implant 2 between the two neighboring vertebrae, it is pushed (pressing tool 30, with which heat or mechanical oscillation may also be transmitted) perpendicularly to the axes of the fasteners 3 against the lateral area of the proximal sides of the fasteners 3 which thereby are connected with the lateral walls of the recesses in the implant. For facilitating the pushing, the recesses in the implant are advantageously laterally staggered and groove-like open at the leading side of the implant (not illustrated).

If the principle illustrated in FIG. 9 is applied to a prosthesis shaft, the bone tissue represented below and above the implant would be the walls of the tubular bone in which the shaft is to be secured, and fasteners would preferably be provided on all sides. If the principle illustrated in FIG. 9 is applied to a tibia plateau implant, the bone tissue represented below the implant is the knee end of the tibia and the tissue represented above the implant is the knee end of the femur or the meniscus respectively. In all named cases the implant side opposite its bone side is not or not easily accessible for applying the pressure and for coupling-in the energy needed for the fastening step.

For anchoring fasteners with the aid of a liquefiable material and mechanical vibration in implantation sites of a limited accessibility as shown in FIGS. 9 and 10, it is advantageous to use a vibrating tool able to redirect the oscillation direction. Such a tool is e.g. described in the publication WO-2007/101362.

FIG. 10 illustrates a further embodiment of the application similar to the one according to FIG. 9, wherein fasteners 3 are not anchored in a direction which is substantially perpendicular to the bone surface but oblique. This embodiment is particularly suitable for securing a prosthesis shaft in a tubular bone but is also suitable e.g. as mentioned above for other implants such as e.g. an intervertebral disk implant or a tibia plateau implant.

Figure 11:
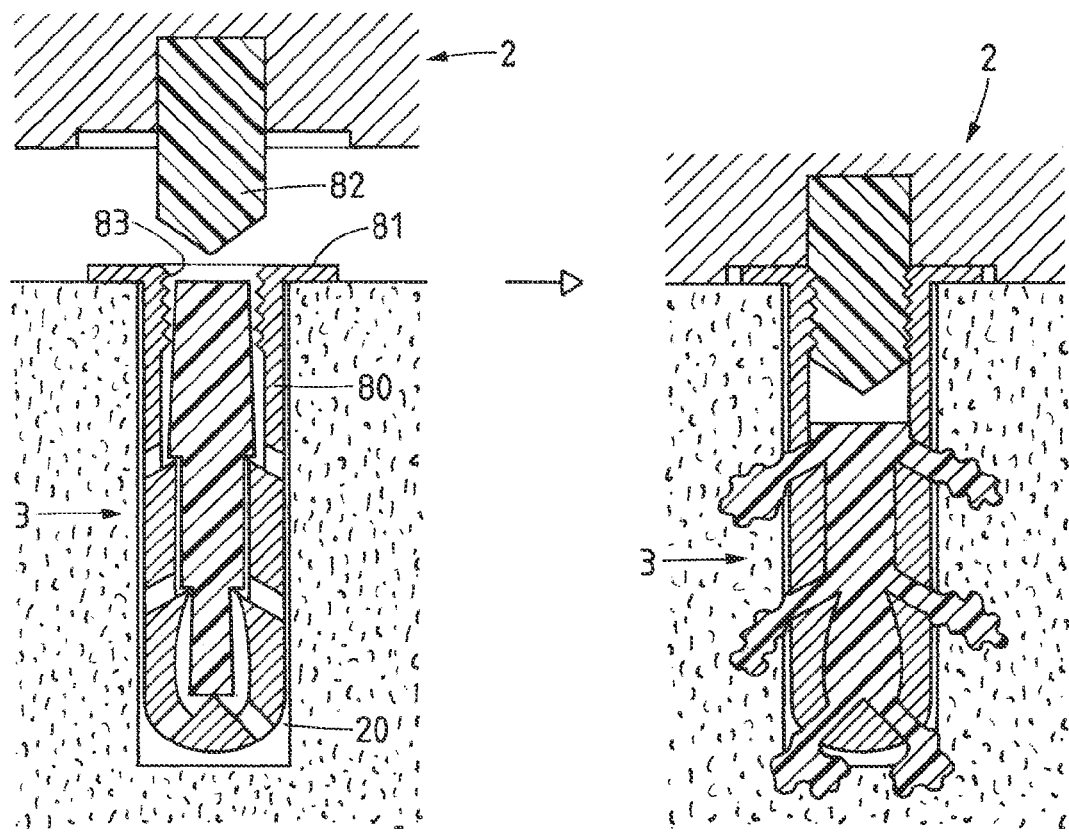
FIGS. 11 to 13 show further exemplary embodiments of fastening structures and fasteners suitable for the implant system according to the invention.

FIG. 11 illustrates the already further above mentioned fastener 3 comprising a sheath 80 and, positioned within the sheath, the liquefiable material which on application of a vibrating tool to the proximal end thereof is liquefied at least partly and is squeezed out of openings provided in the sheath. FIG. 11 shows on the left hand side the fastener which is positioned for being anchored and, above the fastener, a fastening structure of the implant 2 suitable for being fastened to the proximal end of the sheath. On the right hand side, fastener and implant are shown after anchorage of the fastener and securement of the implant on the proximal fastener side.

An opening 20 is provided in the bone tissue and the fastener is positioned therein. If it is desired to prevent the bottom of the opening 20 to be damaged by pressing the sheath into the opening 20, it is suggested to equip the proximal end of the sheath 80 with a flange 81 of a diameter larger than the diameter of the opening 20 and to choose an opening depth which is at least as great as the axial length of the sheath 80. The fastener is anchored in the opening 20 by pressing a vibrating tool (not illustrated) against the proximal end of the liquefiable material and therewith at least partly liquefy the material and pressing it out of the sheath openings into the bone tissue.

The fastening structure of implant 2 comprises a protrusion 82 of a thermoplastic material or being coated therewith, which protrusion has a cross section being slightly larger than the cross section of the mouth region of the sheath. On the inside of this mouth region e.g. a thread 83 or other suitable structure is provided. When the implant 2 is pressed against the proximal side of the sheath and is vibrated simultaneously, the protrusion 82 is forced into the mouth of the sheath 80 whereby the thermoplastic material of the protrusion is liquefied where it gets into contact with the thread 83, is pressed into the thread and forms therewith a positive fit connection on re-solidification.

It may be advantageous to equip the outside surface of the sheath 80 with a surface which is able to do further osseointegration as disclosed in the publication U.S. Pat. No. 7,008, 226 and/or with self cutting edges as disclosed in the publication WO-2005/079696.

FIG. 12 shows an example of a fastener which can be anchored in bone tissue, wherein the proximal fastener end maintains a predetermined position relative to the bone surface, e.g. as illustrated: flush with the bone surface. Again, the fastener 3 is shown on the left hand side when positioned in a corresponding opening 20 for being anchored therein, and on the right side in an anchored configuration with the implant fastened to its proximal side.

The fastener 3 comprises two parts: a tube 85 of a thermoplastic material and a foot piece 86 which may also consist of a thermoplastic material. The foot piece is connected to the distal end of the vibrating tool 87, e.g. screwed thereon, wherein the vibrating tool extends through the tube 85 and through a tube shaped counter element 88. For the anchoring procedure, the vibrating tool 87 with the counter element 88, the tube 85, and the foot piece 86 mounted thereon, is positioned in the opening 20, wherein the counter element 88 is fixed in a position such that its distal end is in the position which is predetermined to be the position of the proximal fastener end after anchorage. The vibrating tool is then pulled in a direction away from the opening 20 and vibrated such that the foot piece 86 pushes the tube 85 against the counter element 88 whereby the material of the tube is liquefied where in contact with the foot piece 86 and penetrates the bone tissue at least in the vicinity, and whereby the tube may be fused to the foot piece. Through the vibration, the foot piece (if consisting of a thermoplastic material) gets warm and therewith soft such that eventually the vibrating tool can be pulled from the foot piece 86, which remains as a part of the anchored fastener in the bone tissue. If the foot piece 86 does not consist of a thermoplastic material, the vibrating tool 87 can, after the anchoring procedure, be separated from the foot by screwing it out or it may be left in place for a proximal end thereof serving for the fastening of the implant.

As shown on the right hand side of FIG. 12, a fastening structure of the implant 2 suitable for being connected with the fastener is e.g. an undercut protrusion 82 of a material which is not liquefiable, the protrusion 82 being forced into the anchored fastener while being vibrated.

Further embodiments of fasteners and anchoring procedures similar to the one illustrated in FIG. 12 are disclosed in the co-pending application U.S. 60/983,791, examples of implantation systems suitable for positioning and anchoring the fastener are disclosed in co-pending application U.S. 61/033,066.

FIG. 13 illustrates a fastener 3 and fastening structures of an implant 2 which are suitable for first positioning the fastener 3 in a bone opening 20, then positioning the implant 2 on the proximal end of the fastener and then applying pressure and vibration to the fastener and therewith anchor the fastener and fasten the implant to the fastener essentially simultaneously. The fastener again comprises a sheath 80 and a liquefiable material therein. The implant 2, comprises as fastening structure, a protrusion with a distal undercut cavity, the cross section of the protrusion being adapted to the inner cross section of the sheath 80. On pressing the implant against the fastener being positioned in the opening 20 and applying mechanical vibration to the implant, the vibrating protrusion 82 is pressed against the liquefiable material inside the sheath, thereby at least partly liquefying it and pressing it out of the sheath into the bone tissue on the one hand and into the cavity of the protrusion on the other hand to form in both places a positive fit connection on re-solidification.

Figure 14B:
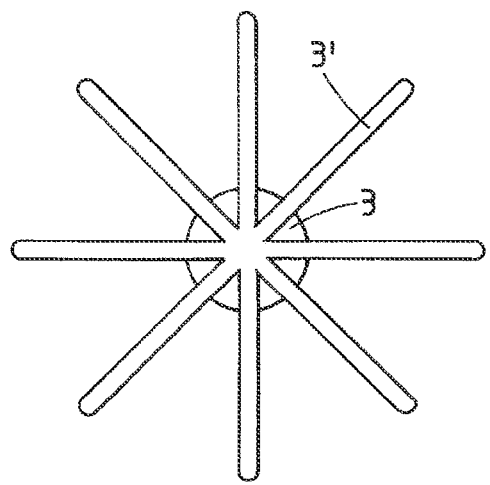
Figure 14C:
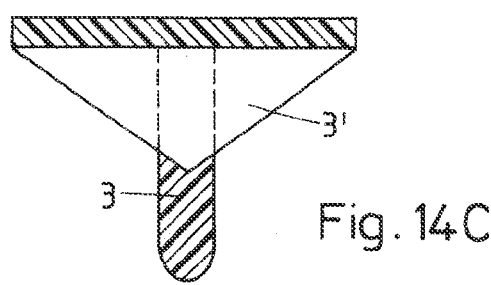

FIGS. 14A to 14C show examples of further fasteners and fastener assemblies which are applicable in the implant system according to the invention.

FIG. 14A shows a blade-shaped fastener. As illustrated in FIG. 1C, such a fastener (3') may replace two, or more than two, pin-shaped fasteners and, if sufficiently long and appropriately shaped, can take over in the sense of a fastener assembly the function of the plurality of fasteners as described above. Such a longish blade-shaped or also tongue-shaped fastener has preferably a curved or folded form (zig-zag or wavy form) or is e.g. closed to form a circle or oval.

The blade shaped fastener illustrated in FIG. 14A having a sharp distal side is suitable for being malleted into the bone tissue. The proximal side comprises a coating of a thermoplastic material and is suitable to be fastened to an implant as shown in FIGS. 1A to 1C. Obviously all other combinations of fastening structures and proximal fastener sides are applicable also for a blade- or tongue-shaped fastener.

FIGS. 14B and 14C show an assembly of a pin-shaped fastener with a plurality of blade-shaped fasteners, wherein the blade shaped fasteners extend radially from a proximal portion of the pin-shaped fastener (FIG. 14B: viewed from the proximal side; FIG. 14C: viewed perpendicular to the pin axis). While the pin-shaped fastener is e.g. made of the thermoplastic material, the blade-shaped fasteners are made of metal and have a sharp distal end and polymer coated proximal heads of a form as shown for the blade-shaped fastener of FIG. 14A. For anchoring the fastener assembly in the bone tissue, an opening corresponding to the pin-shaped fastener is provided and while the pin-shaped fastener is introduced into the opening on being vibrated and therewith anchored, the blade-shaped fasteners cut into the bone tissue to be anchored therein by a press fit. Therein the blade-shaped fasteners are guided by the pin-shaped fastener and the opening in the bone tissue respectively, which guiding constitutes an advantage of the fastener assembly according to FIGS. 14B and 14C as compared with the blade-shaped fastener as shown in FIG. 14A.

In particular for resurfacing implants, where osseointegration of the bone side of the implant is highly desirable, it is important to leave as much of the bone side of the implant in direct contact with the bone tissue and to provide in the bone as little and as small openings as possible, but still to achieve a sufficiently strong fastening of the implant on the bone. For such applications it may be advantageous to use fastener assemblies as shown in FIGS. 14A to 14C.

As already mentioned further above, it is possible to combine anchoring procedures of the fasteners and connecting procedures between the fasteners and the fastening structures of the implant other than illustrated in the above described Figs. Similarly, it is obvious for one skilled in the art that other properties of the embodiments illustrated in the Figs. can be combined in ways different from the combinations which are described explicitly above. Such alternative combinations are also part of the invention.

The invention claimed is:

1. An implant system to be fastened to human or animal bone tissue, the system comprising:

an implant comprising a bone side to be brought into contact with the bone tissue, the bone side of the implant being equipped with a plurality of fastening structures restricted to said bone side; and a plurality of fasteners, each with a distal side and a proximal side, wherein the distal side is equipped for anchoring the fastener in the bone tissue and the proximal side is equipped for a connection with the fastening structures of the implant so that the proximal side of the fastener does not reach to a side of the implant facing away from the bone side, wherein at least one of the following conditions holds:

one of the fastening structures and of the proximal sides of the fasteners comprises undercut recesses and the other one of the fastening structures and of the proximal sides of the fasteners comprises protrusions which are insertable or snappable into the undercut recesses;

one of the fastening structures and of the proximal sides of the fasteners comprises undercut recesses and the other one of the fastening structures and of the proximal sides of the fasteners comprises a thermoplastic material embeddable in the undercut recesses when melted or at least softened;

one of the fastening structures and the proximal sides of the fasteners comprises conical protrusions and the other one of the fastening structures and the proximal sides of the fasteners comprises conical recesses, wherein pressing the conical protrusions into the conical recesses results in a press fit connection;

the fastening structures and the proximal sides of the fasteners comprise thermoplastic material capable of making a material connection, wherein on a side of the implant different from the bone side an axis of application of energy for liquefying the thermoplastic material is defined, and wherein said axis of application of energy is not parallel to an axis of at least one of the fasteners;

wherein the distal sides of the fasteners are equipped with a material which is liquefiable by mechanical oscillation for being anchored with the aid of mechanical oscillation.

2. The system according to claim 1, wherein one of the fastening structures and of the proximal sides of the fasteners comprises undercut recesses.

3. The system according to claim 2, wherein the other one of the fastening structures and of the proximal sides of the fasteners comprises a thermoplastic material embeddable in the undercut recesses when melted or at least softened.

4. The system according to claim 1, wherein one of the fastening structures and the proximal sides of the fasteners comprises conical protrusions and the other one of the fastening structures and the proximal sides of the fasteners comprises conical recesses, wherein pressing the conical protrusions into the conical recesses results in a press fit connection.

5. The system according to claim 1, wherein the fastening structures and the proximal sides of the fasteners comprise thermoplastic material capable of making a material connection.

6. The system according to claim 1, wherein the fastening structures are equipped for being connected to the proximal sides of the fasteners simultaneously.

7. The system according to claim 1, wherein the fasteners are pin-shaped or tongue- or blade-shaped.

8. The system according to claim 1, wherein the implant is a joint implant replacing an articulating surface.

9. The system according to claim 1, wherein the implant is designed for a bone supporting or stabilizing function.

10. An implant system to be fastened to human or animal bone tissue for replacing an articulating surface of a human or animal joint, the system comprising:
 an implant comprising a bone side to be brought into contact with the bone tissue, the bone side of the implant being equipped with a plurality of fastening structures restricted to said bone side, and an articulating surface side, the articulating surface side facing away from the bone side, wherein one of the following conditions holds:
  the articulating surface side forms the articulating surface,
  the articulating surface side comprises a structure for receiving a bearing element, and the implant system further comprises a bearing element shaped to be received by the articulating surface side and forming an articulating surface, the implant system further comprising a plurality of fasteners, each with a distal side and a proximal side, wherein the distal side is equipped for anchoring the fastener in the bone tissue and the proximal side is equipped for a connection with the fastening structures of the implant so that the proximal side of the fastener does not reach to the articulating surface side,
 wherein at least one of the following conditions holds:
  one of the fastening structures and of the proximal sides of the fasteners comprises undercut recesses and the other one of the fastening structures and of the proximal sides of the fasteners comprises protrusions which are insertable or snappable into the undercut recesses;
  one of the fastening structures and of the proximal sides of the fasteners comprises undercut recesses and the other one of the fastening structures and of the proximal sides of the fasteners comprises a thermoplastic material embeddable in the undercut recesses when melted or at least softened;
  one of the fastening structures and the proximal sides of the fasteners comprises conical protrusions and the other one of the fastening structures and the proximal sides of the fasteners comprises conical recesses, wherein pressing the conical protrusions into the conical recesses results in a press fit connection;
 wherein the distal sides of the fasteners are equipped with a material which is liquefiable by mechanical oscillation for being anchored with the aid of mechanical oscillation.

11. The system according to claim 10, wherein the fasteners consist of the liquefiable material.

12. The system according to claim 10, wherein the fasteners comprise a core of a metal, the core being at least partially surrounded by the liquefiable material.

13. The system according to claim 10, wherein the fasteners comprise a perforated sheath and an element of the liquefiable material inserted or insertable in the sheath element.

14. The system according to claim 10 being configured for replacing a tibia plateau or for resurfacing one of a glenoid cavity, an acetabulum, an elbow, wrist, ankle or digital joint, or a femoral head.

15. The system according to claim 10, wherein the implant is made of a metal or a ceramic material or a composite material or a crystalline polymer having a glass transition temperature above 100° C. or a thermosetting polymer.

16. The system according to claim 10 wherein the fastening structures are equipped for being connected to the proximal sides of the fasteners simultaneously.

17. The system according to claim 10, wherein the fasteners are pin-shaped or tongue- or blade-shaped.

18. An implant system to be fastened to human or animal bone tissue, the system comprising:
 an implant comprising a bone side to be brought into contact with the bone tissue, the bone side of the implant being equipped with a plurality of fastening structures restricted to said bone side; and
 a plurality of fasteners, each with a distal side and a proximal side, wherein the distal side is equipped for anchoring the fastener in the bone tissue and the proximal side is equipped for a connection with the fastening structures of the implant so that the proximal side of the fastener does not reach to a side of the implant facing away from the bone side,
 wherein at least one of the following conditions holds:
  one of the fastening structures and of the proximal sides of the fasteners comprises undercut recesses and the other one of the fastening structures and of the proximal sides of the fasteners comprises protrusions which are insertable or snappable into the undercut recesses;
  one of the fastening structures and of the proximal sides of the fasteners comprises undercut recesses and the other one of the fastening structures and of the proximal sides of the fasteners comprises a thermoplastic material embeddable in the undercut recesses when melted or at least softened;
  one of the fastening structures and the proximal sides of the fasteners comprises conical protrusions and the other one of the fastening structures and the proximal sides of the fasteners comprises conical recesses, wherein pressing the conical protrusions into the conical recesses results in a press fit connection;
  the fastening structures and the proximal sides of the fasteners comprise thermoplastic material capable of making a material connection, wherein on a side of the implant different from the bone side an axis of application of energy for liquefying the thermoplastic material is defined, and wherein said axis of application of energy is not parallel to an axis of at least one of the fasteners;

wherein one of the fastening structures and the proximal sides of the fasteners comprises conical protrusions and the other one of the fastening structures and the proximal sides of the fasteners comprises conical recesses, wherein pressing the conical protrusions into the conical recesses results in a press fit connection; wherein the distal sides of the fasteners are equipped with a material which is liquefiable by mechanical oscillation for being anchored with the aid of mechanical oscillation.

19. An implant system to be fastened to human or animal bone tissue, the system comprising:
an implant comprising a bone side to be brought into contact with the bone tissue, the bone side of the implant being equipped with a plurality of fastening structures restricted to said bone side; and
a plurality of fasteners, each with a distal side and a proximal side, wherein the distal side is equipped for anchoring the fastener in the bone tissue and the proximal side is equipped for a connection with the fastening structures of the implant so that the proximal side of the fastener does not reach to a side of the implant facing away from the bone side,
wherein at least one of the following conditions holds:
one of the fastening structures and of the proximal sides of the fasteners comprises undercut recesses and the other one of the fastening structures and of the proximal sides of the fasteners comprises a thermoplastic material embeddable in the undercut recesses when melted or at least softened;
one of the fastening structures and the proximal sides of the fasteners comprises conical protrusions and the other one of the fastening structures and the proximal sides of the fasteners comprises conical recesses, wherein pressing the conical protrusions into the conical recesses results in a press fit connection;
the fastening structures and the proximal sides of the fasteners comprise thermoplastic material capable of making a material connection, wherein on a side of the implant different from the bone side an axis of application of energy for liquefying the thermoplastic material is defined, and wherein said axis of application of energy is not parallel to an axis of at least one of the fasteners;
wherein the implant is a joint implant replacing an articulating surface; wherein the distal sides of the fasteners are equipped with a material which is liquefiable by mechanical oscillation for being anchored with the aid of mechanical oscillation.

20. The system according to claim 18, wherein the distal sides of the fasteners are equipped with a thread for being anchored by screwing.

21. The system according to claim 19, wherein the distal sides of the fasteners are equipped with a pointed or sharp end for being malleted into the bone tissue.

22. The system according to claim 19, wherein the implant is a tibia plateau replacement implant.

23. The system according to claim 19, wherein the implant is a resurfacing implant for a glenoid cavity, for an acetabulum, for an elbow, wrist, ankle or digital joint, or for a femoral head.

24. A kit of parts, the kit comprising:
an implant system according to claim 19 and
further comprising a template with a bone side adapted to the bone side of the implant and with through bores in positions corresponding with the positions of the fastening structures on the implant and/or a pressing tool being adapted to a joint side of the implant.

25. The system according to claim 19, wherein the other one of the fastening structures and of the proximal sides of the fasteners comprises a thermoplastic material embeddable in the undercut recesses when melted or at least softened.

26. The system according to claim 19, wherein one of the fastening structures and the proximal sides of the fasteners comprises conical protrusions and the other one of the fastening structures and the proximal sides of the fasteners comprises conical recesses, wherein pressing the conical protrusions into the conical recesses results in a press fit connection.

27. The system according to claim 19, wherein the fastening structures and the proximal sides of the fasteners comprise thermoplastic material capable of making a material connection.

28. The system according to claim 19, wherein the fastening structures are equipped for being connected to the proximal sides of the fasteners simultaneously.

29. The system according to claim 19, wherein the fasteners are pin-shaped or tongue- or blade-shaped.

* * * * *